(12) United States Patent
Blom et al.

(10) Patent No.: US 11,219,729 B2
(45) Date of Patent: Jan. 11, 2022

(54) MEDICAL DEVICE SYSTEM AND METHOD INCLUDING AN ENDOTRACHEAL TUBE

(71) Applicant: Hansa Medical Products, Inc., Carmel, IN (US)

(72) Inventors: Eric D. Blom, Carmel, IN (US); Brian Kamradt, Indianapolis, IN (US)

(73) Assignee: Hansa Medical Products, Inc., Carmel, IN (US)

( * ) Notice: Subject to any disclaimer, the term of this patent is extended or adjusted under 35 U.S.C. 154(b) by 0 days.

(21) Appl. No.: 16/980,789

(22) PCT Filed: Mar. 21, 2019

(86) PCT No.: PCT/US2019/023346
§ 371 (c)(1),
(2) Date: Sep. 14, 2020

(87) PCT Pub. No.: WO2019/183338
PCT Pub. Date: Sep. 26, 2019

(65) Prior Publication Data
US 2020/0405990 A1     Dec. 31, 2020

Related U.S. Application Data

(60) Provisional application No. 62/646,169, filed on Mar. 21, 2018.

(51) Int. Cl.
*A61M 16/04*     (2006.01)
*A61M 25/06*     (2006.01)

(52) U.S. Cl.
CPC .... *A61M 16/0488* (2013.01); *A61M 16/0434* (2013.01); *A61M 16/0463* (2013.01); *A61M 16/0486* (2014.02); *A61M 2025/0681* (2013.01)

(58) Field of Classification Search
CPC .......................................... A61M 16/04–0486
See application file for complete search history.

(56) References Cited

U.S. PATENT DOCUMENTS

| 1,598,283 | A | 8/1926 | Kinney |
| 2,892,458 | A | 6/1959 | Auzin |

(Continued)

FOREIGN PATENT DOCUMENTS

| DE | 25 05 123 A1 | 1/1976 |
| DE | 34 06 294 | 9/1985 |

(Continued)

OTHER PUBLICATIONS

English-language abstract of JPH 09501084A, 1 page, (see U.S. Pat. No. 5,390,669 for English-language equivalent).

(Continued)

*Primary Examiner* — LaToya M Louis
(74) *Attorney, Agent, or Firm* — Barnes & Thornburg LLP

(57) ABSTRACT

A medical device system and method including an endotracheal tube configured for insertion into a patients mouth or nose are disclosed. The endotracheal tube may include an outer cannula extending from a proximal end to a distal end configured to be positioned between in a patient's trachea. The outer cannula may include a lumen extending from a first opening defined in the proximal end to a second opening defined in the distal end. The endotracheal tube may further include an inner cannula removably positioned in the lumen of the outer cannula. The inner cannula may include a proximal end that extends outwardly from the first opening of the outer cannula, a distal end positioned adjacent to the distal end of the outer cannula, and a passageway extending through the distal and proximal ends of the inner cannula.

32 Claims, 7 Drawing Sheets

(56) References Cited

U.S. PATENT DOCUMENTS

| | | | |
|---|---|---|---|
| 3,688,774 | A | 9/1972 | Akiyama |
| 3,996,939 | A | 12/1976 | Sheridan et al. |
| 4,022,219 | A | 5/1977 | Basta |
| 4,211,234 | A | 7/1980 | Fisher |
| 4,223,411 | A | 9/1980 | Schoendorfer et al. |
| 4,280,492 | A | 7/1981 | Latham |
| 4,304,228 | A | 12/1981 | Depel |
| 4,305,392 | A | 12/1981 | Chester |
| 4,315,505 | A | 2/1982 | Crandall et al. |
| 4,327,721 | A | 5/1982 | Goldin et al. |
| 4,449,523 | A | 5/1984 | Szachowicz et al. |
| 4,459,984 | A | 7/1984 | Liegner |
| 4,469,100 | A | 9/1984 | Hardwick |
| 4,573,460 | A | 3/1986 | Szachowicz et al. |
| 4,584,998 | A | 4/1986 | McGrail |
| 4,589,410 | A | 5/1986 | Miller |
| 4,596,248 | A | 6/1986 | Lieberman |
| 4,607,635 | A | 8/1986 | Heyden |
| 4,617,015 | A | 10/1986 | Foltz |
| 4,627,433 | A | 12/1986 | Lieberman |
| 4,632,108 | A | 12/1986 | Geil |
| 4,637,389 | A | 1/1987 | Heyden |
| 4,762,125 | A | 8/1988 | Leiman et al. |
| 4,834,087 | A | 5/1989 | Coleman et al. |
| 4,840,173 | A | 6/1989 | Porter, III |
| 4,852,565 | A | 8/1989 | Eisele |
| 5,056,515 | A | 10/1991 | Abel |
| 5,067,497 | A | 11/1991 | Greear et al. |
| 5,107,828 | A | 4/1992 | Koss et al. |
| 5,132,922 | A | 6/1992 | Berg |
| 5,201,310 | A | 4/1993 | Turnbull |
| 5,217,008 | A | 6/1993 | Lindholm |
| 5,218,970 | A | 6/1993 | Turnbull et al. |
| 5,255,676 | A | 10/1993 | Russo |
| 5,297,546 | A | 3/1994 | Spofford et al. |
| 5,329,921 | A | 7/1994 | Socaris et al. |
| 5,339,808 | A | 8/1994 | Don Mchael |
| 5,343,857 | A | 9/1994 | Schneider et al. |
| 5,349,950 | A | 9/1994 | Ulrich et al. |
| 5,390,669 | A | 2/1995 | Stuart et al. |
| 5,391,205 | A | 2/1995 | Knight |
| 5,392,775 | A | 2/1995 | Adkins |
| 5,458,139 | A | 10/1995 | Pearl |
| 5,497,768 | A | 3/1996 | Lomholt |
| 5,507,279 | A | 4/1996 | Fortune et al. |
| 5,515,844 | A | 5/1996 | Christopher |
| 5,584,288 | A | 12/1996 | Baldwin |
| 5,599,333 | A | 2/1997 | Atkinson |
| RE35,595 | E | 8/1997 | Six |
| 5,687,767 | A | 11/1997 | Bowers |
| 5,688,256 | A | 11/1997 | Surratt et al. |
| 5,746,199 | A | 5/1998 | Bayron et al. |
| 5,771,888 | A | 6/1998 | Keim |
| 5,819,723 | A * | 10/1998 | Joseph ............... A61M 16/044 128/207.14 |
| 5,957,978 | A | 9/1999 | Blom |
| 6,053,167 | A | 4/2000 | Waldeck |
| 6,089,225 | A | 7/2000 | Brown et al. |
| 6,102,038 | A | 8/2000 | Devries |
| 6,105,577 | A | 8/2000 | Varner |
| 6,135,110 | A | 10/2000 | Roy |
| 6,135,111 | A | 10/2000 | Mongeon |
| 6,254,591 | B1 | 7/2001 | Roberson |
| 6,463,927 | B1 | 10/2002 | Pagan |
| 6,722,367 | B1 | 4/2004 | Blom |
| 6,814,077 | B1 | 11/2004 | Eistert |
| 7,404,329 | B2 | 7/2008 | Quinn et al. |
| 7,681,576 | B2 * | 3/2010 | Thomas ............... A61M 16/04 128/207.29 |
| 7,987,851 | B2 | 8/2011 | Blom |
| 8,707,956 | B2 | 4/2014 | Blom |
| 9,579,477 | B2 | 2/2017 | Blom |
| 2003/0084905 | A1 | 5/2003 | Ortiz |
| 2004/0079376 | A1 | 4/2004 | Melker |
| 2004/0123868 | A1 | 7/2004 | Rutter |
| 2005/0205097 | A1 | 9/2005 | Kyle |
| 2008/0257353 | A1 | 10/2008 | Yamamoto et al. |
| 2009/0260632 | A1 | 11/2009 | Abnousi et al. |
| 2011/0011406 | A1 | 1/2011 | Blom et al. |
| 2012/0247473 | A1 | 10/2012 | Fendler |
| 2013/0098358 | A1 | 4/2013 | Blom et al. |
| 2013/0269704 | A1 | 10/2013 | Thomas et al. |
| 2015/0209534 | A1 | 7/2015 | Bruggeman et al. |
| 2017/0065781 | A1 * | 3/2017 | Field ............... A61M 16/0427 |
| 2017/0165441 | A1 | 6/2017 | Blom et al. |
| 2018/0169363 | A1 | 6/2018 | Blom et al. |

FOREIGN PATENT DOCUMENTS

| | | |
|---|---|---|
| DE | 37 20 482 A1 | 12/1988 |
| DE | 38 13 705 A1 | 1/1989 |
| DE | 195 13 831 C1 | 5/1996 |
| DE | 101 09 935 | 11/2001 |
| EP | 0 489 516 A1 | 6/1992 |
| EP | 1803478 A1 | 7/2007 |
| JP | S59135064 A | 8/1984 |
| JP | S628766 A | 1/1987 |
| JP | H04272771 A | 9/1992 |
| JP | H09290023 A | 11/1997 |
| JP | H1076010 A | 3/1998 |
| JP | H115602143 A | 2/1999 |
| JP | 2002210014 A | 7/2002 |
| JP | 2007521926 | 8/2007 |
| JP | 2011194222 A | 10/2011 |
| WO | 99/07428 A1 | 2/1999 |
| WO | 99/12599 | 3/1999 |
| WO | 00/32262 | 6/2000 |
| WO | 2005077449 A1 | 8/2005 |
| WO | 2005112796 A2 | 12/2005 |
| WO | 2008027575 A1 | 3/2008 |

OTHER PUBLICATIONS

International Search Report from PCT/US2013/072237 dated Feb. 7, 2014, 8 pages.

Quick Reference Guide to Shiley's "Quality-Of Life" Line of Tracheostomy Products, 1991.

Granuloma Associated with Fenestrated Tracheostomy Tubes, Padmanabhan Siddharth, MD, PhD, FACS and lawrence Mazzarella, MD, FACS, Case Reports, vol. 150, Aug. 1985, pp. 279-280.

Tracheostomy and Laryngectomy Tubes, pp. 568 and 572, datd unknown, published before Dec. 27, 2005.

Tracheostomy Tube Adult Home Care Guide, Shiley Tracheostomy Products, mallinckrodt Medical pp. 1-40, date unknown, published before Dec. 27, 2005.

D. Hessler, MD, K. Rehder, MD and S.W. Karveth, MD, "Tracheostomy Cannula for Speaking During Artificial Respiration", Anesthesiology, vol. 25, No. 5, pp. 719-721, 1964.

Technical Support Information Connections with the Passy-Muir Tracheostomy and Ventilator Speaking Valves, one sheet, date unknown, published before Dec. 27, 2005.

European Search Report from EP 06 02 0526 dated Apr. 19, 2007.

Charles G. Durbin, MD, "Tracheostomy: Why, When, and How?", Respitory Care, Aug. 2010, 13 pages.

USPTO, International Search Report from PCT/US2019/023346, dated Jun. 10, 2019, 3 pages.

USPTO, Written Opinion of the Searching Authority from PCT/US2019/023346, dated Jun. 10, 2019, 7 pages.

* cited by examiner

110

| Size | Endotracheal Tube 10 ||| Inner Cannula 14 |||| Outer Cannula 12 |||
|---|---|---|---|---|---|---|---|---|---|---|
| | Inner Radius 96 | Outer Radius 88 | Wall Thickness 104 | Inner Radius 96 | Outer Radius 92 | Wall Thickness 100 | Inner Radius 90 | Outer Radius 88 | Wall Thickness 102 |
| 7 | 3.50 | 5.00 | 0.75 | 3.50 | 4.00 | 0.25 | 4.00 | 5.00 | 0.50 |
| 7.5 | 3.75 | 5.25 | 0.75 | 3.75 | 4.25 | 0.25 | 4.25 | 5.25 | 0.50 |
| 8 | 4.00 | 5.50 | 0.75 | 4.00 | 4.50 | 0.25 | 4.50 | 5.50 | 0.50 |
| 8.5 | 4.25 | 5.75 | 0.75 | 4.25 | 4.75 | 0.25 | 4.75 | 5.75 | 0.50 |
| 9 | 4.50 | 6.00 | 0.75 | 4.50 | 5.00 | 0.25 | 5.00 | 6.00 | 0.50 |
| 9.5 | 4.75 | 6.25 | 0.75 | 4.75 | 5.25 | 0.25 | 5.25 | 6.25 | 0.50 |
| 10 | 5.00 | 6.50 | 0.75 | 5.00 | 5.50 | 0.25 | 5.50 | 6.50 | 0.50 |

| Size | Inner Cannula Wall Cross-Sectional Area 122 | Tube Overall Cross-Sectional Area 124 | Outer Cannula Wall Cross-Sectional Area 126 | Tube Total Wall Cross-Sectional Area 128 |
|---|---|---|---|---|
| 7 | 11.78 | 78.54 | 28.27 | 40.06 |
| 7.5 | 12.57 | 86.59 | 29.85 | 42.41 |
| 8 | 13.35 | 95.03 | 31.42 | 44.77 |
| 8.5 | 14.14 | 103.87 | 32.99 | 47.12 |
| 9 | 14.92 | 113.10 | 34.56 | 49.48 |
| 9.5 | 15.71 | 122.72 | 36.13 | 51.84 |
| 10 | 16.49 | 132.73 | 37.70 | 54.19 |

Fig. 5

| Size | Assembly 210 | | | Inner Cannula 214 | | | Outer Cannula 212 | | |
|---|---|---|---|---|---|---|---|---|---|
| | Inner Radius 316 | Outer Radius 328 | Wall Thickness 344 | Inner Radius 316 | Outer Radius 312 | Wall Thickness 320 | Inner Radius 340 | Outer Radius 328 | Wall Thickness 342 |
| 7 | 3.50 | 5.00 | 0.75 | 3.50 | 4.00 | 0.25 | 4.00 | 5.00 | 0.50 |
| 7.5 | 3.75 | 5.25 | 0.75 | 3.75 | 4.25 | 0.25 | 4.25 | 5.25 | 0.50 |
| 8 | 4.00 | 5.50 | 0.75 | 4.00 | 4.50 | 0.25 | 4.50 | 5.50 | 0.50 |
| 8.5 | 4.25 | 5.75 | 0.75 | 4.25 | 4.75 | 0.25 | 4.75 | 5.75 | 0.50 |
| 9 | 4.50 | 6.00 | 0.75 | 4.50 | 5.00 | 0.25 | 5.00 | 6.00 | 0.50 |
| 9.5 | 4.75 | 6.25 | 0.75 | 4.75 | 5.25 | 0.25 | 5.25 | 6.25 | 0.50 |
| 10 | 5.00 | 6.50 | 0.75 | 5.00 | 5.50 | 0.25 | 5.50 | 6.50 | 0.50 |

MEDICAL DEVICE SYSTEM AND METHOD INCLUDING AN ENDOTRACHEAL TUBE

CROSS-REFERENCE TO RELATED APPLICATIONS

This application is a U.S. national stage entry of PCT International Patent Application No. PCT/US2019/023346, filed Mar. 21, 2019, which claims priority to and the benefit of U.S. Provisional Patent Application No. 62/646,169, filed Mar. 21, 2018, the entire disclosures of which are incorporated herein by reference.

TECHNICAL FIELD

The present disclosure relates, generally, to medical devices and methods and, in particular, to endotracheal tubes such as, for example, orotracheal tubes and nasotracheal tubes.

BACKGROUND

A tracheal tube is typically a catheter that is inserted into the trachea for the purpose of providing an airway for a patient. An endotracheal tube is a specific type of tracheal tube that is inserted through the mouth (orotracheal) or nose (nasotracheal). Such endotracheal tubes are in contrast to a tracheostomy tube, which is inserted into a tracheostoma following a tracheostomy procedure, and a tracheal button, which may also be inserted into a puncture through the paratracheal skin into the trachea.

An endotracheal tube may be cuffed or uncuffed. Cuffed endotracheal tubes include a cuff that can be inflated to minimize the passage of secretions from the upper respiratory tract downward into the lungs of a patient.

The following are of interest: U.S. Pat. Nos. 1,598,283; 2,892,458; 3,688,774; 3,996,939; 4,211,234; 4,223,411; 4,280,492; 4,304,228; 4,305,392; 4,315,505; 4,327,721; 4,449,523; 4,459,984; 4,469,100; 4,573,460; 4,584,998; 4,589,410; 4,596,248; 4,607,635; 4,627,433; 4,632,108; 4,637,389; 4,762,125; 4,834,087; 4,840,173; 4,852,565; 5,056,515; 5,067,497; 5,107,828; 5,123,922; 5,201,310; 5,217,008; 5,218,970; 5,255,676; 5,297,546; 5,329,921; 5,339,808; 5,343,857; 5,349,950; 5,391,205; 5,392,775; 5,458,139; 5,497,768; 5,507,279; 5,515,844; 5,584,288; 5,599,333; RE35,595; 5,687,767; 5,688,256; 5,746,199; 5,771,888; 5,957,978; 6,053,167; 6,089,225; 6,102,038; 6,105,577; 6,135,110; 6,135,111; 6,463,927; 6,722,367; 6,814,007; 7,404,329; 8,573,220; 9,579,477; U.S. Patent Publication Nos: 2003/0084905; 2004/0123868; 2016/028239; 2016/0102312; 2017/0014589; foreign/international patent publications: DE 25 05 123; DE 34 06 294; DE 37 20 482; DE 38 13 705; DE 195 13 831; DE 101 09 935; WO 99/07428; WO 99/12599; WO 00/32262; WO2015/136232; other publications: Design and Development of Ultrathin-walled, Nonkinking Endotracheal Tubes of a New "No-Pressure" Laryngeal Seal Design, Anesthesiology, Vol. 81, 1061-1067 (1994). No representation is intended by this listing that a thorough search of all material prior art has been conducted, or that no better art than that listed is available.

SUMMARY

According to one aspect of the present disclosure, a medical device system and method including an endotracheal tube configured for insertion into a patient's mouth or nose are disclosed. The endotracheal tube may include an outer cannula extending from a proximal end to a distal end configured to be positioned between in a patient's trachea. The outer cannula may include a lumen extending from a first opening defined in the proximal end to a second opening defined in the distal end. The endotracheal tube may further include an inner cannula removably positioned in the lumen of the outer cannula. The inner cannula may include a proximal end that extends outwardly from the first opening of the outer cannula, a distal end positioned adjacent to the distal end of the outer cannula, and a passageway extending through the distal and proximal ends of the inner cannula.

When the endotracheal tube is viewed in cross-section, the endotracheal tube has a total cross-sectional area, the outer cannula has a first wall thickness and an outer cannula cross-sectional wall area, and the inner cannula has a second wall thickness and an inner cannula cross-sectional wall area. In some embodiments, a first ratio defined between the outer cannula cross-sectional wall area and the total cross-sectional area of the endotracheal tube may be less than or equal to 0.40. In some embodiments, a second ratio defined between the inner cannula cross-sectional wall area and the total cross-sectional area of the endotracheal tube may be greater than or equal to 0.12. In some embodiments, the second wall thickness of the inner cannula may be less than the first wall thickness of the outer cannula.

Additional aspects of the present disclosure are discussed below and defined in the appended claims.

BRIEF DESCRIPTION OF THE DRAWINGS

The detailed description particularly refers to the following figures, in which:

FIGS. 4 and 5 are tables of one embodiment of dimensions and areas for a family of endotracheal tubes;

DETAILED DESCRIPTION OF THE DRAWINGS

Figure 1:
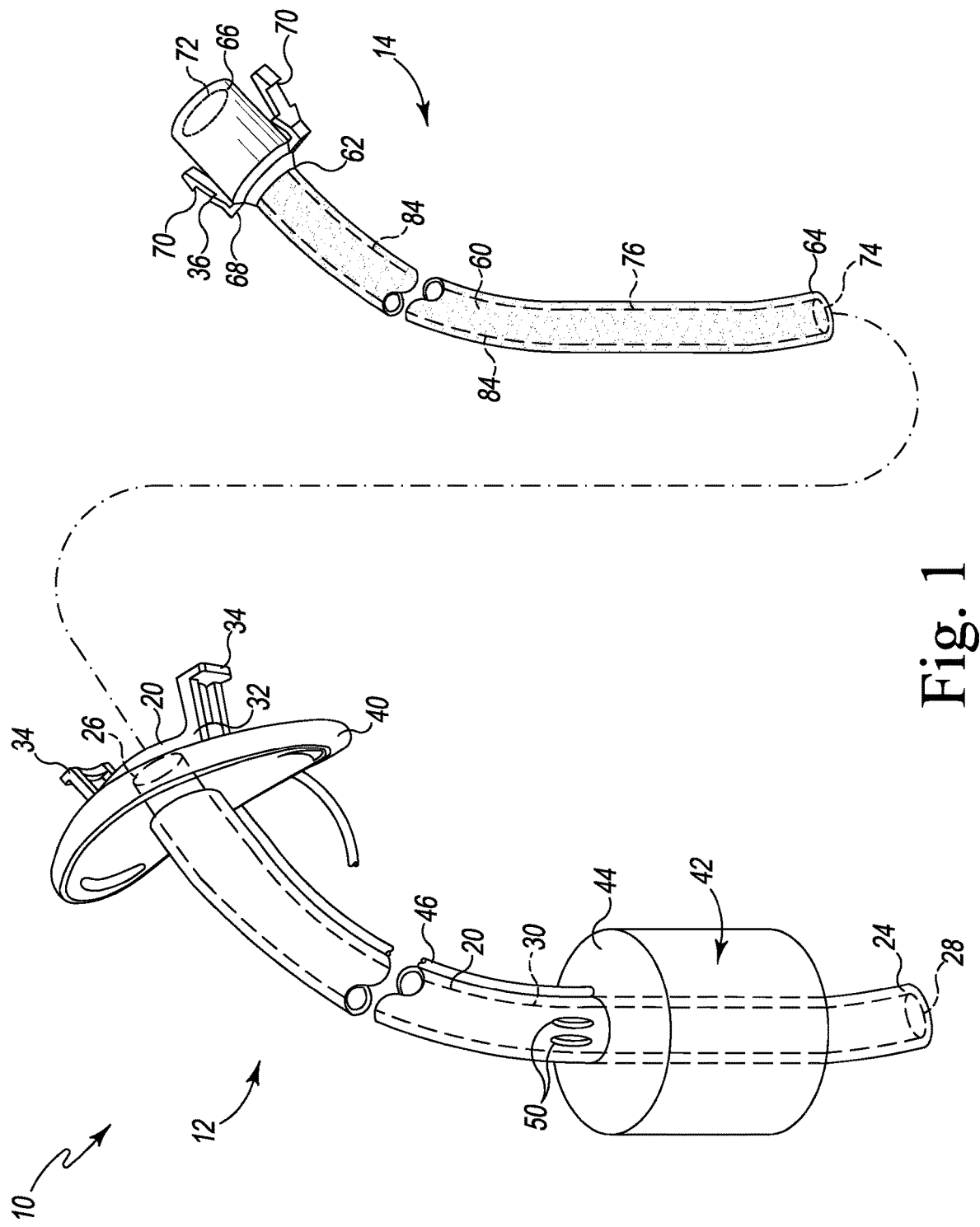
FIG. 1 is an exploded perspective view of an endotracheal tube for use in a medical device system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the surgical tools and medical instruments described herein as well as in reference to the patient's natural anatomy. Such terms have well-understood meanings in both the study of anatomy and the field of medical devices. Use of such anatomical reference terms in the written description and claims is intended to be consistent with their well-understood meanings unless noted otherwise.

Referring now to FIG. 1, a medical device system including an endotracheal tube 10 is shown. In the illustrative embodiment, the tube 10 is an orotracheal tube configured for insertion through a patient's mouth into the patient's trachea. It should be appreciated that the structure and techniques described herein may be used with a nasotracheal tube as well. The endotracheal tube 10 includes an outer endotracheal cannula 12 and an inner elongated cannula 14 configured to be inserted into the outer cannula 12.

The outer endotracheal cannula 12 includes an elongated curved body 20 that extends from a proximal end 22 to a distal end 24. The curved body 20 has a circular opening 26 defined in the proximal end 22 and another circular opening 28 defined in the opposite distal end 24. A lumen 30 extends between the openings 26, 28 and has a curvature corresponding to the curvature of the body 20. In the illustrative embodiment, the lumen has a circular cross-section along its length. In other embodiments, the openings 26, 28 may be, for example, oval or oblong, and the lumen may have an oval or oblong cross-section. The cannula 12 is semi-rigid and formed from a biocompatible plastic resin such as, for example, polyvinyl carbonate, but it should be appreciated that in other embodiments other suitable materials may be used.

The outer endotracheal cannula 12 has a rim 32 that extends outwardly from the proximal end 22. A pair of locking flanges 34 extend outwardly from the rim 32 on opposite sides of the proximal opening 26. As described in greater detail below, the flanges 34 are sized to receive corresponding locking tabs 36 of the inner cannula 14 to secure the inner cannula 14 to the outer cannula 12. In the illustrative embodiment, the rim 32, the locking flanges 34, and the elongated curved body 20 are formed as a single monolithic component. It should be appreciated that in other embodiments they may be formed as separate components that are later assembled.

As shown in FIG. 1, a guard plate 40 is attached to the elongated curved body 20 adjacent to the proximal end 22. In the illustrative embodiment, the guard plate 40 is attached via a pair of pivot pins (not shown) that permit limited movement of the guard plate 40 relative to the rest of the outer cannula 12. The guard plate 40 is oblong and sized to be positioned over a patient's mouth to keep the proximal end 22 of the outer cannula 12 outside of and offset from the patient's mouth when in use. The guard plate 40 is also formed from a biocompatible plastic resin and in the illustrative embodiment is semi-flexible.

In the illustrative embodiment, an inflatable cuff 42 is attached to the curved body 20 near the distal end 24 such that the cuff 42 lies in the patient's trachea during use. As shown in FIG. 1, the cuff 42 includes a sleeve 44 formed from silicone or other flexible material. The cuff 42 is inflatable through a conduit 46 that extends from the cuff 42 along the outer surface of the curved body 20 and beyond the proximal end 22. As described in greater detail below, the cuff 42 is inflatable through the conduit 46 when positioned in the patient's trachea to minimize the passage of secretions from the upper respiratory tract downward into the lungs of the patient. It should be appreciated that in other embodiments the inflatable cuff may be omitted.

As shown in FIG. 1, the outer cannula 12 includes a number of openings or fenestrations 50 that are positioned proximal of the inflatable cuff 42. Although two openings 50 are shown in FIG. 1, it should be understood that in other embodiments additional or fewer openings 50 may be included in the cannula 12. In still other embodiments, the openings may be omitted.

As described above, the endotracheal tube 10 also includes an inner elongated cannula 14 configured for insertion into the outer cannula 12. As shown in FIG. 1, the inner cannula 14 includes a body 60 that extends from a proximal end 62 to a distal end 64. The inner cannula 14 also includes a port 66 that extends proximally from the proximal end 62 of the body 60. A mounting flange 68 extends outwardly from the proximal end 62. A pair of locking tabs 36 extend outwardly and proximally from the mounting flange 68. Each tab 36 includes a raised edge 70 configured to engage a corresponding locking flange 34 of the outer endotracheal cannula 12 to secure the inner cannula 14 in the outer cannula 12.

The inner cannula 14 as a proximal opening 72 defined in the port 66 and an opposite distal opening 74 defined in the end 64 of the body 60. A passageway 76 extends between the openings 72, 74 and is sized to permit the passage of oxygen and other gases from a ventilator (not shown) or other medical device attached to the port 66 downward into the patient's lungs. The passageway 76 has a circular cross-section along its length. In other embodiments, the openings 72, 74 may be, for example, oval or oblong, and the passageway may have an oval or oblong cross-section. In the illustrative embodiment, the body 60 and the port 66 are formed as a single semi-flexible monolithic component from a biocompatible plastic resin. In that way, the body 60 conforms to the shape of the curved lumen 30 of the outer cannula 12 when the body 60 is positioned in the lumen 30. In the illustrative embodiment, the flange 68 and locking tabs 36 are rigid and formed separately from biocompatible plastic resin.

In the illustrative embodiment, the body 60 of the inner elongated cannula 14 has a curved outer surface 80 that extends from the proximal end 62 to the distal end 64. The curved outer surface 80 is textured such that it has a roughened surface finish to break the surface tension between the curved outer surface 80 of the inner cannula 14 and the inner wall 82 (see FIG. 3) of the outer cannula 12. In the illustrative embodiment, the texture on the outer surface 80 includes a number of etchings 84, which may be formed by bead-blasting the outer surface 80 of the body 60.

Although only a single inner cannula 14 is shown in FIG. 1, the endotracheal tube 10 includes multiple such cannulas 14 so that the inner elongated cannula may be replaced as needed and with less difficulty and without the trauma that might accompany the replacement of the outer cannula 12. It should be appreciated that the endotracheal tube 10 may include other inner cannulas of different configurations, which are sized to be positioned separately in the outer cannula 12. For example, the endotracheal tube 10 may include an inner cannula having one or more openings positioned between its proximal and distal ends. The openings may be positioned such that secretions pooling at the fenestrations 50 of the outer cannula 12 may be exposed to suction, as described in greater detail below.

Figure 2:
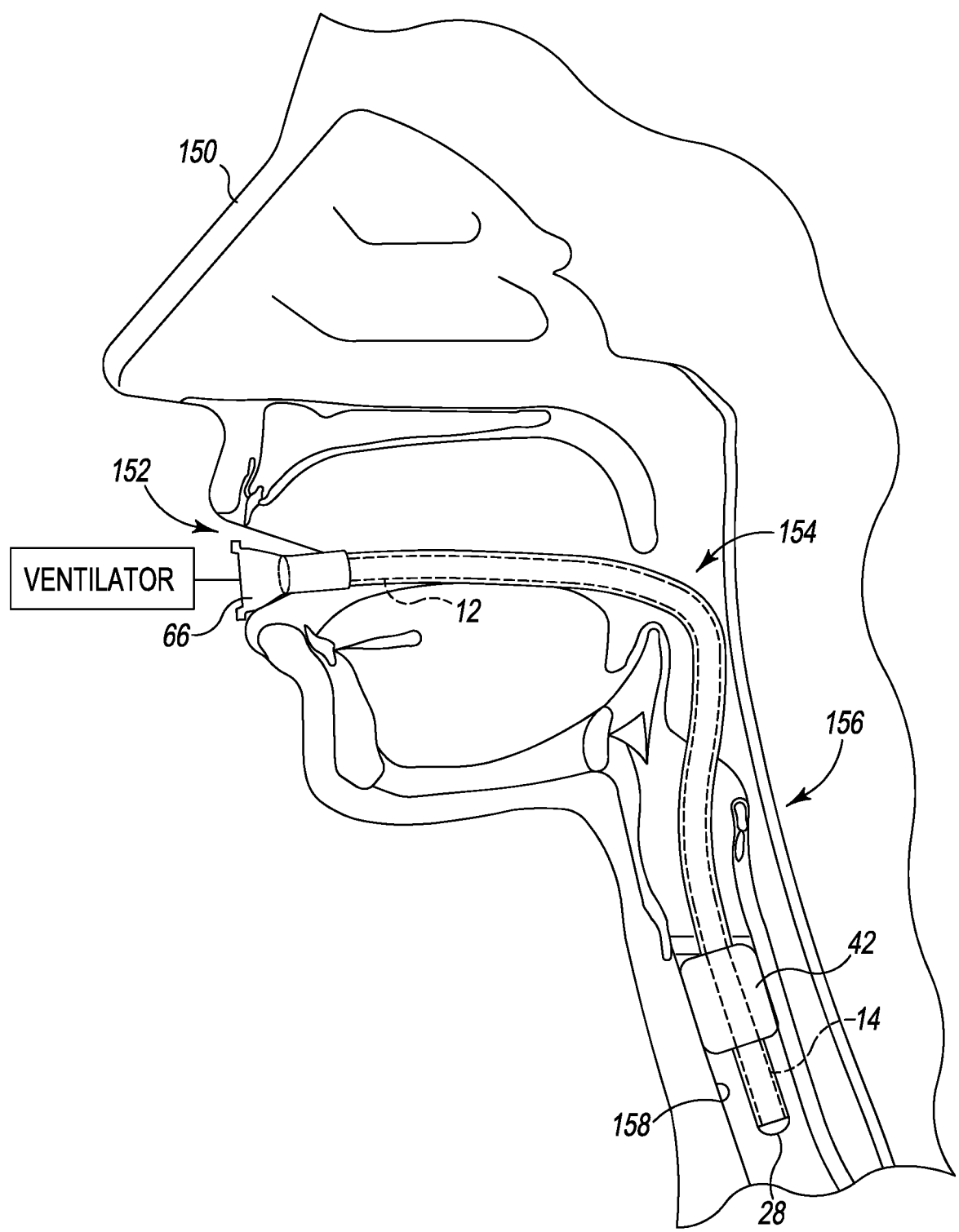
FIG. 2 is cross-sectional side elevation view showing the endotracheal tube of FIG. 1 positioned in a patient's body.

Referring now to FIG. 2, a patient 150 requiring an endotracheal tube is shown. The outer cannula 12 extends through the mouth 152 of the patient 150, down the patient's pharynx 154, and through the patient's glottis 156 so that the distal opening 28 of the cannula 12 is positioned in the patient's trachea 158 above the patient's carina (not shown). In the illustrative embodiment, the cannula 12 is about 320 millimeters in length to permit the distal opening 28 to be properly positioned in the patient's trachea 158. As described above, the inflatable cuff 42 is attached to the curved body 20 of the endotracheal cannula 12 and is positioned so that the cuff 42 lies in the trachea 158 below the glottis 156 when positioned as shown in FIG. 2.

The inner elongated cannula 14 is shown positioned in the lumen 30 of the outer cannula 12. When positioned with its locking tabs 36 engaged with the flanges 34 of the endotracheal cannula 12, the distal opening 74 of the inner cannula 14 is positioned adjacent to the distal opening 28 of the cannula 12. In the illustrative embodiment, the cannula 14 is about 300 millimeters in length to permit the distal opening 74 to be properly positioned relative to the distal opening 28. It should be appreciated that the length of the cannulas 12, 14 may vary depending on the type and size of patient. As shown in FIG. 2, a ventilator or other device may be coupled to the port 66 of the inner cannula 14 to provide oxygen or other gases to the patient 150.

Figure 3:
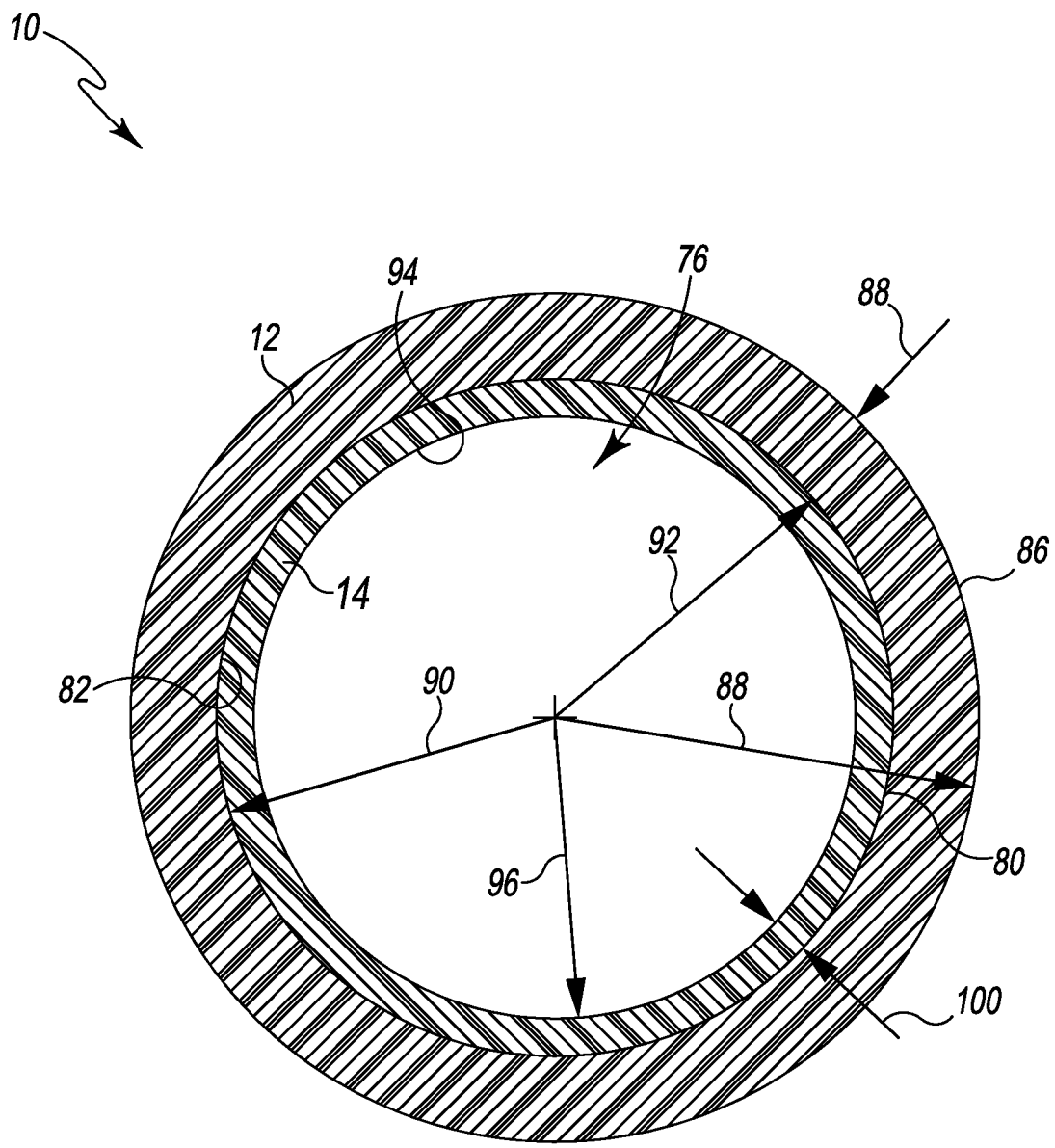
FIG. 3 is a cross-sectional elevation view of the endotracheal tube taken along the line 3-3 in FIG. 2.

Referring now to FIG. 3, the outer cannula 12 includes a curved outer surface 86 that extends from the proximal end 22 of its curved body 20 to the distal end 24. The outer surface 86 of the outer cannula 12 defines the outer surface of the endotracheal tube 10. When viewed in cross-section as shown in FIG. 3, the outer surface 86 has an outer radius 88, which is the outer radius of the endotracheal tube 10. In the illustrative embodiment, the outer radius 88 is constant along the length of the cannula 12.

As described above, the outer cannula 12 also includes an inner wall 82 that defines the lumen 30 in the curved body 20. When viewed in cross-section as shown in FIG. 3, the inner wall 82 has an inner radius 90, which is the radius of the lumen 30. In the illustrative embodiment, the inner radius 90 is constant along the length of the cannula 12.

As described above, the inner elongated cannula 14 includes an outer surface 80 that confronts the inner wall 82 of the endotracheal cannula 12. When viewed in cross-section as shown in FIG. 3, the outer surface 80 has an outer radius 92, which is the outer radius of the inner cannula 14. In the illustrative embodiment, the outer radius 92 is constant along the length of the cannula 14.

The inner cannula 14 also includes an inner wall 94 that defines the passageway 76 of the inner cannula 14. When viewed in cross-section as shown in FIG. 3, the inner wall 94 has an inner radius 96, which is the inner radius of the endotracheal tube 10. In the illustrative embodiment, the inner radius 96 is constant along the length of the cannula 14. It should be appreciated that in other embodiments the radii 88, 90, 92, 96 may be tapered.

The inner cannula 14 also has a wall thickness 100 that is defined between the inner wall 94 and the outer surface 80, while the wall thickness 102 of the endotracheal cannula 12 is defined between the inner wall 82 and the outer surface 86. It should be appreciated that the wall thicknesses 100, 102 are constant along the lengths of the cannulas 12, 14 in the illustrative embodiment. In other embodiments, the wall thicknesses may be tapered. As shown in FIG. 4, the total wall thickness 104 of the endotracheal tube 10 is defined by the sum of the wall thicknesses 100, 102.

Referring now to FIG. 4, a table 110 including dimensions for the medical device system is shown for a family of endotracheal tubes. As shown in FIG. 4, dimensions for a range of sizes of endotracheal tubes from Size 7 to Size 10 are identified in millimeters (mm). It should be appreciated that the dimensions shown in the table 110 are exemplary only and that in other embodiments may be different values depending on the patient anatomy or the materials of the cannulas 12, 14. The dimensions also should be understood to encompass a manufacturing tolerance of ±0.2 mm. Similarly, the terms "about," "substantially," and other terms of relative degree used in this specification should be understood to refer to ranges within typical manufacturing tolerances, including, for example, ±0.2 mm.

Endotracheal tube systems are required to be flexible and soft enough to conform to the patient's anatomy without exerting undue pressure on the body tissues but must be of sufficient strength to resist collapse and kinking when in use. Endotracheal tube systems must also permit sufficient gas flow to properly ventilate a patient. In the illustrative embodiment, the endotracheal tube 10 utilizes the combined properties of the cannulas 12, 14 to satisfy these requirements for each size of endotracheal tube. To do so, the endotracheal tube 10 is designed so that the inner cannula 12 is large enough to contribute to the performance of the overall tube 10 (e.g., the ratio of the inner cannula wall thickness to the tube outer radius or the ratio of the inner cannula wall cross-sectional area to the overall cross-sectional area of the tube is not too little or small). In other words, for example, the inner cannula is sized to have sufficient strength to support the endotracheal tube 10 when inserted into the patient's trachea and have a passageway 76 that is sized to permit proper ventilation.

The endotracheal tube 10 is also designed so that the outer cannula 12 is not too large for a given tube size (e.g., the ratio of the outer cannula wall thickness to the tube outer radius or the ratio of the outer cannula wall cross-sectional area to the overall cross-sectional area of the tube is not too great). In other words, for example, if the outer cannula has too great an outer radius, the outer cannula may not properly conform to a patient's anatomy. Additionally, if the outer cannula has too large a wall thickness, the resulting inner cannula may be too small for proper performance. On the other hand, if the outer cannula has too thin a wall thickness, the overall endotracheal tube may not have sufficient strength.

Accordingly, in the illustrative embodiment, the inner cannula 14 and the outer cannula 12 are designed such that the ratio of the inner cannula wall thickness 100 to the outer radius 88 of the tube is between 0.08 and 0.10. The ratio of the outer cannula wall thickness 102 to the tube outer radius 88 is between 0.15 and 0.21. It should be appreciated that the ratio of the inner cannula wall thickness 100 to the outer cannula wall thickness 102 is equal to about 0.50 (i.e., the inner cannula wall thickness 100 is about half of the outer cannula wall thickness 102).

Referring now to FIG. 5, a table 120 of exemplary cross-sectional areas of the cannulas 12, 14 for a family of endotracheal tube assemblies including a number of sizes. All units are in millimeters-squared ($mm^2$). In the illustrative embodiment, the inner cannula wall cross-sectional area 122 was calculated based on the inner radius 96 and the outer radius 92 of the inner cannula 14. Similarly, the outer cannula wall cross-sectional area 126 was calculated based on the inner radius 90 and the outer radius 88 of the outer cannula 12. The values in table 120 for the overall cross-sectional area 124 of the endotracheal tube 10 were calculated using the outer radius 88 of the outer cannula 12. The values in table 120 for the total cross-sectional wall area 128 of the endotracheal tube 10 were calculated using the inner radius 96 of the inner cannula 14 and the outer radius 88 of the outer cannula 12.

In the illustrative embodiment, the ratio of the inner cannula wall cross-sectional area 122 to the overall cross-sectional area 124 of the tube 10 is between 0.12 and 0.15. The ratio of the outer cannula wall cross-sectional area 126 to the overall cross-sectional area 124 of the endotracheal tube 10 is between 0.25 and 0.40. In one particular embodiment, the ratio of the outer cannula wall cross-sectional area 126 to the overall cross-sectional area 124 of the endotracheal tube is between 0.28 and 0.36. Additionally, the ratio of the outer cannula wall cross-sectional area 126 to the total cross-sectional wall area 128 of the endotracheal tube 10 is about 0.70.

Figure 6:
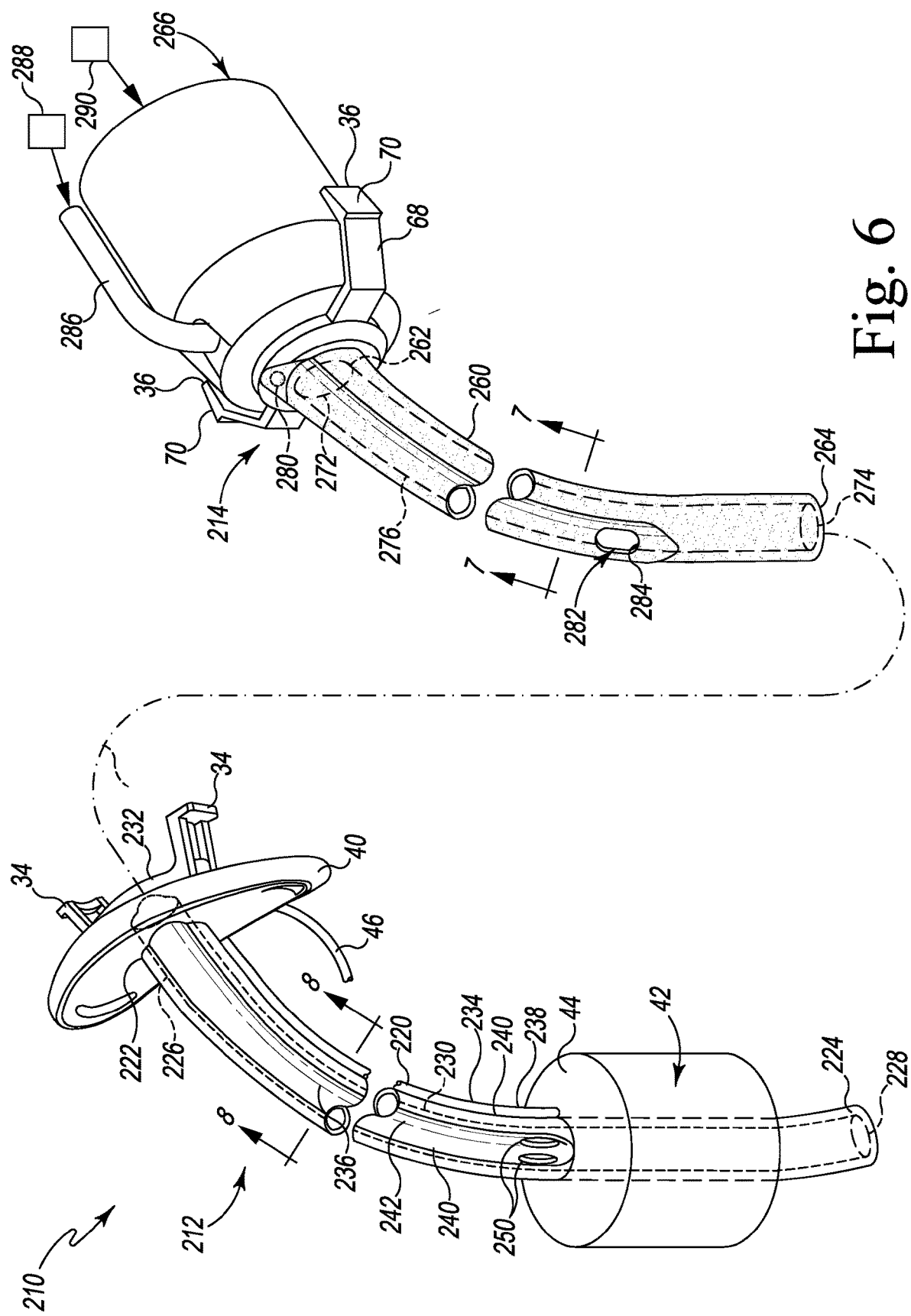
FIG. 6 is an exploded perspective view of another endotracheal tube for use in a medical device system.

Referring now to FIGS. 6-10, another embodiment of an endotracheal tube (hereinafter endotracheal tube 210) of a medical device system is shown. As described in greater detail below, the endotracheal tube 210 is structured to permit removal of secretions that might pool on the proximal end of the inflatable cuff 42, Some of the features of the endotracheal tube 210 are similar to the features of endotracheal tube 10. The reference numbers from FIGS. 1-5 are used to identify similar features in FIGS. 6-10. Referring now to FIG. 6, the endotracheal tube 210 includes an outer endotracheal cannula 212 and an inner elongated cannula 214 configured to be inserted into the outer cannula 212.

The outer endotracheal cannula 212 includes an elongated curved body 220 that extends from a proximal end 222 to a distal end 224. The curved body 220 has an opening 226 defined in the proximal end 222 and another opening 228 defined in the opposite distal end 224. A lumen 230 extends between the openings 226, 228 and has a curvature corresponding to the curvature of the body 220. The cannula 212 is semi-rigid and formed from a biocompatible plastic resin such as, for example, polyvinyl carbonate, but it should be appreciated that in other embodiments other suitable materials may be used.

The outer endotracheal cannula 212 has a rim 232 that extends outwardly from the proximal end 222. A pair of locking flanges 34 extend outwardly from the rim 232 on opposite sides of the proximal opening 26. As described in greater detail below, the flanges 34 are sized to receive corresponding locking tabs 36 of the inner cannula 214 to secure the inner cannula 214 to the outer cannula 212. In the illustrative embodiment, the rim 232, the locking flanges 34, and the elongated curved body 220 are formed as a single monolithic component. It should be appreciated that in other embodiments they may be formed as separate components that are later assembled.

As shown in FIG. 6, a guard plate 40 is attached to the elongated curved body 220 adjacent to the proximal end 222. In the illustrative embodiment, the guard plate 40 is attached via a pair of pivot pins (not shown) that permit limited movement of the guard plate 40 relative to the rest of the outer cannula 212. The guard plate 40 is oblong and sized to be positioned over a patient's mouth to keep the proximal end 222 of the outer cannula 212 outside of and offset from the patient's mouth when in use. The guard plate 40 is also formed from a biocompatible plastic resin and in the illustrative embodiment is semi-flexible.

The elongated curved body 220 of the outer cannula 212 has a central body section 234 that extends between the ends 222, 224 and an outer body section 236 that extends from the central body section 234. The central body section 234 includes a curved outer surface 238 that extends around the body section 234 between a pair of longitudinal edges 240.

The outer body section 236 includes a curved outer surface 242 that is also connected to the edges 240, as shown in FIG. 6.

In the illustrative embodiment, an inflatable cuff 42 is attached to the curved body 220 near the distal end 224 such that the cuff 42 lies in the patient's trachea during use. As shown in FIG. 6, the cuff 42 is positioned distal of the outer body section 236 of the cannula 212. The cuff 42 includes a sleeve 44 formed from silicone or other flexible material. The cuff 42 is inflatable through a conduit 46 that extends from the cuff 42 along the outer surface of the curved body 220 and beyond the proximal end 222. As described in greater detail below, the cuff 42 is inflatable through the conduit 46 when positioned in the patient's trachea to minimize the passage of secretions from the upper respiratory tract downward into the lungs of the patient. It should be appreciated that in other embodiments the inflatable cuff may be omitted.

As shown in FIG. 6, the outer cannula 212 includes a number of openings or fenestrations 250 that defined in the curved outer surface 242 of the outer body section 236. The fenestrations 250 are positioned proximal of the inflatable cuff 42 in the illustrative embodiment. Although two openings 250 are shown in FIG. 6, it should be understood that in other embodiments additional or fewer openings 250 may be included in the cannula 212. In still other embodiments, the openings may be omitted.

As described above, the endotracheal tube 210 also includes an inner elongated cannula 214 configured for insertion into the outer cannula 212. As shown in FIG. 6, the inner cannula 214 includes a body 260 that extends from a proximal end 262 to a distal end 264. The inner cannula 214 also includes a port 266 that extends proximally from the proximal end 262 of the body 260. A mounting flange 68 extends outwardly from the proximal end 262. A pair of locking tabs 36 extend outwardly and proximally from the mounting flange 268. Each tab 36 includes a raised edge 70 configured to engage a corresponding locking flange 34 of the outer endotracheal cannula 212 to secure the inner cannula 214 in the outer cannula 212. In the illustrative embodiment, the flange 68 and locking tabs 36 are rigid and formed separately from biocompatible plastic resin.

The inner cannula 214 has a proximal opening 272 defined in the port 266 and an opposite distal opening 274 defined in the end 264 of the body 260. A passageway 276 extends between the openings 272, 274 and is sized to permit the passage of oxygen and other gases from a ventilator (not shown) or other medical device attached to the port 66 downward into the patient's lungs. The passageway 276 has a circular cross-section along its length. In other embodiments, the openings 272, 274 may be, for example, oval or oblong, and the passageway may have an oval or oblong cross-section.

Figure 7:
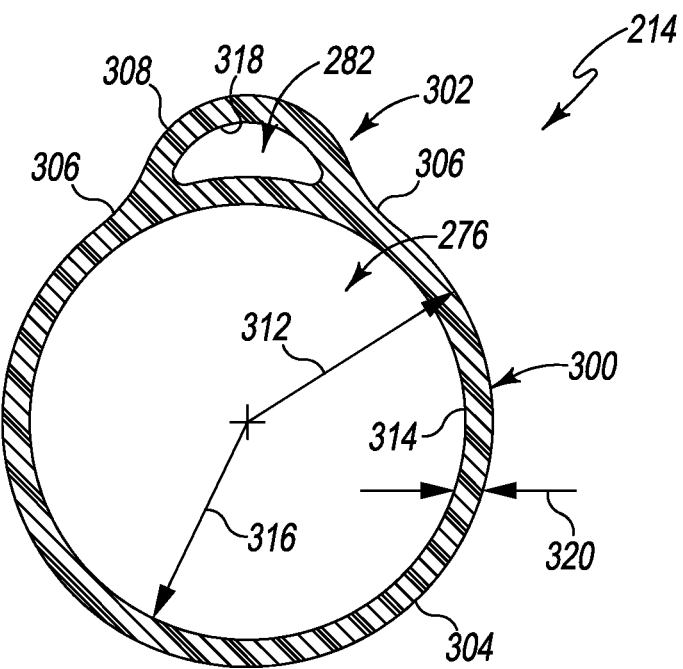
FIG. 7 is a cross-sectional elevation view of an inner cannula of the endotracheal tube taken along the line 7-7 in FIG. 6.

The inner cannula 214 has another proximal opening 280 defined in the proximal end 262 of the body 260 and another passageway 282 extends distally from the opening 280 to a distal opening 284 positioned between the proximal end 262 and the distal end 264 of the body 260. As shown in FIG. 7, the passageway 282 is spaced apart and separated from the other passageway 276 of the inner cannula 214. In the illustrative embodiment, the distal opening 284 of the passageway 282 is sized and positioned to be aligned with the fenestrations 250 of the outer cannula 212 to permit suction of any secretions that might pool on the cuff 42.

Returning to FIG. 6, a conduit 286 connected to the passageway 282 extends from the inner cannula 214. The conduit 286 is configured to be coupled to a negative pressure source 288 to create suction within the passageway 282. A ventilator or other device 290 may be coupled to the port 266 of the inner cannula 214 to provide oxygen or other gases to the patient. In the illustrative embodiment, the body 260, port 266, and conduit 286 are formed as a single semi-flexible component from a biocompatible plastic resin. The body 260 is configured to conform to the shape of the curved lumen 230 of the outer cannula 212 when the body 260 is positioned in the lumen 230.

The elongated curved body 260 of the inner cannula 214 has a central body section 300 that extends between the ends 262, 264 and an outer body section 302 that extends from the central body section 300. As shown in FIG. 7, the central body section 300 includes a curved outer surface 304 that extends around the body section 300 between a pair of longitudinal edges 306. The outer body section 302 includes a curved outer surface 308 that is also connected to the edges 306. The curved outer surfaces 304, 308 are textured such that it has a roughened surface finish to break the surface tension between the curved outer surfaces 304, 308 of the inner cannula 214 and the inner wall 310 (see FIG. 8) of the outer cannula 212. In the illustrative embodiment, the texture on the outer surfaces 304, 308 includes a number of etchings, which may be formed by bead-blasting the outer surfaces 304, 308 of the body 260.

When viewed in cross-section as shown in FIG. 7, the outer surface 304 has an outer radius 312, which is the outer radius of the central body section 300 of the inner cannula 214. In the illustrative embodiment, the outer radius 312 is constant along the length of the cannula 214.

The inner cannula 214 also includes an inner wall 314 that defines the passageway 276 of the inner cannula 214. When viewed in cross-section as shown in FIG. 7, the inner wall 314 has an inner radius 316, which is the inner radius of the endotracheal tube 210. In the illustrative embodiment, the inner radius 316 is constant along the length of the cannula 214. It should be appreciated that in other embodiments the radii 312, 316 may be tapered.

As shown in FIG. 7, the inner wall 314 separates the inner passageway 276 from the suction passageway 282 of the inner cannula 214. The inner cannula 214 also includes an inner wall 318 that extends from the proximal opening 280 to the distal opening 284 to define the suction passageway 282.

The inner cannula 214 also has a wall thickness 320 that is defined between the inner wall 314 and the outer surface 304. It should be appreciated that the wall thicknesses 320 is constant along the length of the cannulas 214 in the illustrative embodiment. In other embodiments, the wall thickness may be tapered.

Figure 8:
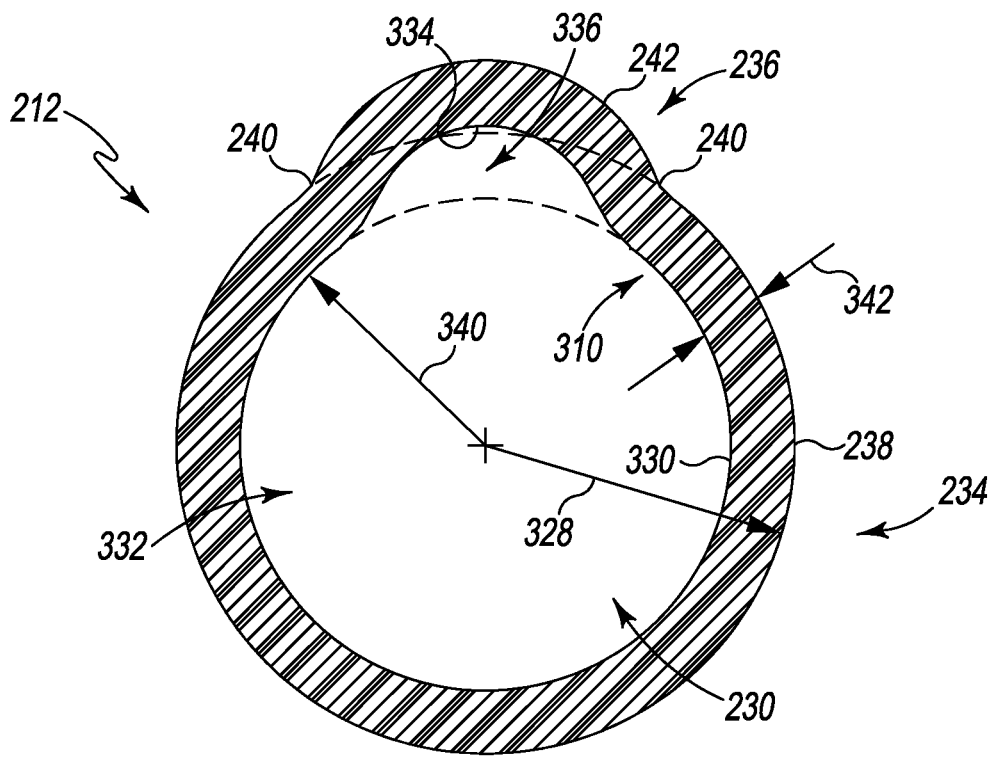
FIG. 8 is a cross-sectional elevation view of an outer cannula of the endotracheal tube taken along the line 8-8 in FIG. 6.

Referring now to FIG. 8, the outer cannula 212 includes the curved outer surface 238 that extends from the proximal end 222 of its curved body 220 to the distal end 224. The outer surface 238 of the outer cannula 212 defines a portion of the outer surface of the endotracheal tube 210. When viewed in cross-section as shown in FIG. 8, the outer surface 238 has an outer radius 328, which is the outer radius of the central section of the endotracheal tube 210. In the illustrative embodiment, the outer radius 328 is constant along the length of the cannula 12.

As described above, the outer cannula 212 also includes an inner wall 310 that defines the lumen 230 in the curved body 220. The inner wall 310 includes an inner surface 330 that defines a central section 332 of the lumen 230 sized to receive the central body section 300 of the inner cannula 214. The inner wall 310 also includes an inner surface 334 that defines an outer section 336 of the lumen 230. The outer lumen section 336 opens into the central lumen section 332 and is sized to receive the outer body section 302 of the inner cannula 214, as shown in FIG. 9.

When viewed in cross-section as shown in FIG. 8, inner surface 330 has an inner radius 340, which is the radius of the central lumen section 332. In the illustrative embodiment, the inner radius 340 is constant along the length of the cannula 212. The outer cannula 214 also has a wall thickness 342 that is defined between the inner surface 330 and the outer surface 238, which is constant along the length of the cannula 212 in the illustrative embodiment. In other embodiments, the wall thickness may be tapered. As shown in FIG. 9, the total wall thickness 344 of the endotracheal tube 210 is defined by the sum of the wall thicknesses 320, 342.

Figures 9, 10:
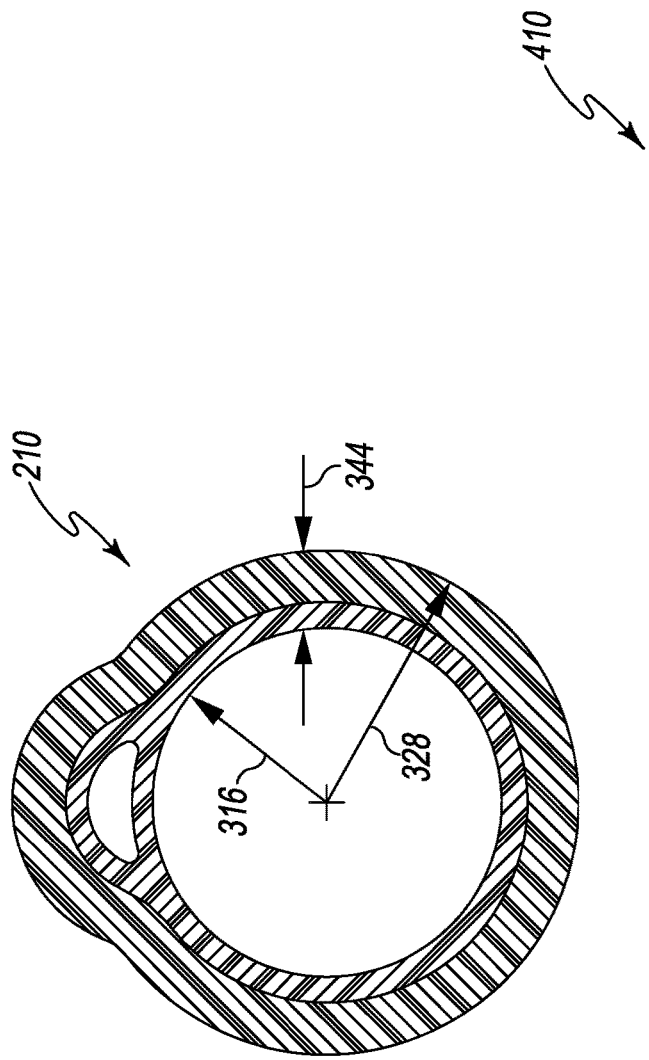
FIG. 9 is a cross-sectional elevation view of the endotracheal tube with the inner cannula positioned in the outer cannula.
FIG. 10 is a table of another embodiment of dimensions for a family of endotracheal tubes.

Referring now to FIG. 10, a table 410 including dimensions for the medical device system is shown for a family of endotracheal tubes. As shown in FIG. 10, dimensions for a range of sizes of endotracheal tubes from Size 7 to Size 10 are identified in millimeters (mm). It should be appreciated that the dimensions shown in the table 410 are exemplary only and that in other embodiments may be different values depending on the patient anatomy or the materials of the cannulas 212, 214. Similar to the embodiment of FIGS. 1-5, endotracheal tube 210 utilizes the combined properties of the cannulas 212, 214 to satisfy the various endotracheal tube requirements for each size of endotracheal tube.

In the illustrative embodiment, the inner cannula 214 and the outer cannula 212 are designed such that the ratio of the inner cannula wall thickness 320 to the outer radius 328 of the tube is between 0.08 and 0.10. The ratio of the outer cannula wall thickness 342 to the tube outer radius 328 is between 0.15 and 0.21. It should be appreciated that the ratio of the inner cannula wall thickness 320 to the outer cannula wall thickness 342 is equal to about 0.50 (i.e., the inner cannula wall thickness 320 is about half of the outer cannula wall thickness 342).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. A medical device, comprising:
   an endotracheal tube configured for insertion into a patient's mouth or nose, comprising:
   an outer cannula extending from a proximal end to a distal end configured to be positioned in a patient's trachea, the outer cannula including a lumen extending from a first opening defined in the proximal end to a second opening defined in the distal end, and
   an inner cannula removably positioned in the lumen of the outer cannula, the inner cannula having (i) a proximal end that extends outwardly from the first opening of the outer cannula, (ii) a distal end positioned adjacent to the distal end of the outer cannula, and (iii) a passageway extending between the distal and proximal ends of the inner cannula, wherein, when the endotracheal tube is viewed in cross-section, the endotracheal tube has a total cross-sectional area, the outer cannula has an outer cannula cross-sectional wall area, and the inner cannula has an inner cannula cross-sectional wall area, wherein a first ratio is defined between the outer cannula cross-sectional wall area and the total cross-sectional area of the endotracheal tube, the first ratio being less than or equal to 0.40, and wherein a second ratio is defined between the inner cannula cross-sectional wall area and the total cross-sectional area of the endotracheal tube, the second ratio being greater than or equal to 0.12.

2. The medical device of claim 1, wherein the first ratio is in a range of 0.25 to 0.40.

3. The medical device of claim 2, wherein the first ratio is in a range of 0.28 to 0.36.

4. The medical device of claim 1, wherein the second ratio is in a range of 0.12 to 0.15.

5. The medical device of claim 1, wherein, when the endotracheal tube is viewed in cross-section, the endotracheal tube has a total cross-sectional wall area that is a sum of the outer cannula cross-sectional wall area and the inner cannula cross-sectional wall area, and a third ratio is defined between the outer cannula cross-sectional wall area and the total cross-sectional wall area, the third ratio being equal to about 0.70.

6. The medical device of claim 1, wherein:
the outer cannula has a curved inner wall that defines the lumen and has a first radius,
the inner cannula has a curved outer surface that extends from the proximal end to the distal end of the inner cannula, the curved outer surface has a second radius that is substantially equal to the first radius, and
the curved outer surface of the inner cannula is textured.

7. The medical device of claim 1, wherein the outer cannula cross-sectional wall area and the inner cannula cross-sectional wall area are constant along the endotracheal tube.

8. The medical device of claim 1, further comprising a first port coupled to the proximal end of the outer cannula and a second port coupled to the proximal end of the inner cannula.

9. The medical device of claim 1, further comprising an inflatable cuff coupled to the outer cannula.

10. The medical device of claim 9, wherein a fenestration is defined in the outer cannula adjacent to a proximal surface of the inflatable cuff.

11. The medical device of claim 10, wherein the passageway of the inner cannula is a first inner passageway, and the inner cannula includes a second inner passageway that is spaced apart from the first inner passageway, the second inner passageway having an opening aligned with the fenestration of the outer cannula to evacuate a region of the patient's trachea adjacent the inflatable cuff.

12. A medical device comprising:
an endotracheal tube configured for insertion into a patient's mouth or nose, comprising:
an outer cannula extending from a proximal end to a distal end configured to be positioned in a patient's trachea, the outer cannula including a lumen extending from a first opening defined in the proximal end to a second opening defined in the distal end, and
an inner cannula removably positioned in the lumen of the outer cannula, the inner cannula having (i) a proximal end that extends outwardly from the first opening of the outer cannula, (ii) a distal end positioned adjacent to the distal end of the outer cannula, and (iii) a passageway extending between the distal and the proximal ends of the inner cannula, wherein, when the endotracheal tube is viewed in cross-section, the outer cannula has a first wall thickness and the inner cannula has a second wall thickness that is less than the first wall thickness of the outer cannula, wherein, when the endotracheal tube is viewed in cross-section, the outer cannula includes an outer surface that is defined by a first radius, wherein a first ratio is defined between the first wall thickness and the first radius, the first ratio being less than or equal to 0.21, and wherein a second ratio is defined between the second wall thickness and the first radius, the second ratio being greater than or equal to 0.08.

13. The medical device of claim 12, wherein the first ratio is in a range of 0.15 to 0.21.

14. The medical device of claim 13, wherein the second ratio is in a range of 0.08 to 0.10.

15. The medical device of claim 12, wherein the inner cannula has a curved outer surface that extends from the proximal end to the distal end of the inner cannula, and the curved outer surface of the inner cannula is textured.

16. The medical device of claim 12, further comprising an inflatable cuff coupled to the outer cannula.

17. The medical device of claim 16, wherein a fenestration is defined in the outer cannula adjacent to a proximal surface of the inflatable cuff.

18. The medical device of claim 17, wherein the passageway of the inner cannula is a first inner passageway, and the inner cannula includes a second inner passageway that is spaced apart from the first inner passageway, the second inner passageway having an opening aligned with the fenestration of the outer cannula to evacuate a region of the patient's trachea adjacent the inflatable cuff.

19. A medical device comprising:
an endotracheal tube configured for insertion into a patient's mouth or nose, comprising:
an outer cannula extending from a proximal end to a distal end configured to be positioned in a patient's trachea, the outer cannula including a lumen extending from a first opening defined in the proximal end to a second opening defined in the distal end, and
an inner cannula removably positioned in the lumen of the outer cannula, the inner cannula having (i) a proximal end that extends outwardly from the first opening of the outer cannula, (ii) a distal end positioned adjacent to the distal end of the outer cannula, and (iii) a passageway extending between the distal and the proximal ends of the inner cannula, wherein, when the endotracheal tube is viewed in cross-section, the outer cannula has a first wall thickness and the inner cannula has a second wall thickness that is less than the first wall thickness of the outer cannula, wherein, when the endotracheal tube is viewed in cross-section, the endotracheal tube has an overall cross-sectional area, the outer cannula has an outer cannula cross-sectional wall area, and the inner cannula has an inner cannula cross-sectional wall area, wherein a first ratio is defined between the outer cannula cross-sectional wall area and the overall cross-sectional area of the endotracheal tube, the first ratio being less than or equal to 0.4, and wherein a second ratio is defined between the inner cannula cross-sectional wall area and the outer cross-sectional area of the endotracheal tube, the second ratio being greater than or equal to 0.12.

20. The medical device of claim 19, wherein the first ratio is in a range of 0.25 to 0.40.

21. The medical device of claim 20, wherein the first ratio is in a range of 0.28 to 0.36.

22. The medical device of claim 21, wherein the second ratio is in a range of 0.12 to 0.15.

23. The medical device of claim 19, wherein, when the endotracheal tube is viewed in cross-section, the endotracheal tube has a total cross-sectional wall area that is a sum of the outer cannula cross-sectional wall area and the inner cannula cross-sectional wall area, and a third ratio is defined between the outer cannula cross-sectional wall area and the total cross-sectional wall area, the third ratio being equal to about 0.7.

24. The medical device of claim 19, wherein:
the first wall thickness of the outer cannula is defined between (i) a first outer surface extending between the distal and proximal ends of the outer cannula and (ii) a first inner surface positioned opposite the first outer surface, the first outer surface having a first radius, and
the outer cannula includes a second outer surface that is connected to the first outer surface and extends between the distal and proximal ends of the outer cannula, the second outer surface having a second radius that is less than the first radius.

25. The medical device of claim 24, wherein:
the outer cannula includes a second inner surface that is connected to the first inner surface and is positioned opposite the second outer surface, and
the first inner surface of the outer cannula defines a central section of the lumen, and
the second inner surface of the outer cannula defines an outer section of the lumen that opens into the central section.

26. The medical device system of claim 19, wherein the inner cannula has a curved outer surface that extends from the proximal end to the distal end of the inner cannula, and the curved outer surface is textured.

27. A medical device comprising:
an outer cannula extending from a proximal end to a distal end configured to be positioned in a patient's trachea, the outer cannula including a lumen extending from a first opening defined in the proximal end to a second opening defined in the distal end, and an inner cannula configured to be positioned in the lumen of the outer cannula, the inner cannula having (i) a proximal end that is configured to extend outwardly from the first opening of the outer cannula, (ii) a distal end is configured to be positioned adjacent to the distal end of the outer cannula, and (iii) a passageway extending between the distal and the proximal ends of the inner cannula, wherein, when the inner cannula and the outer cannula are viewed in cross-section, the outer cannula has a first wall thickness and the inner cannula has a second wall thickness that is less than the first wall thickness of the outer cannula, wherein, when the outer cannula is viewed in cross-section, the outer cannula has an outer cross-sectional area, the outer cannula has an outer cannula cross-sectional wall area, and a first ratio is defined between the outer cannula cross-sectional wall area and the outer cross-sectional area, the first ratio being less than or equal to 0.40, and wherein, when the inner cannula is viewed in cross-section, the inner cannula has an inner cannula cross-sectional wall area, and a second ratio is defined between the inner cannula cross-sectional wall area and the outer cross-sectional area of the outer cannula, the second ratio being greater than or equal to 0.12.

28. The medical device system of claim 27, wherein the first ratio is in a range of 0.25 to 0.4.

29. The medical device system of claim 28, wherein the first ratio is in a range of 0.28 to 0.36.

30. The medical device system of claim 28, wherein the second ratio is in a range of 0.12 to 0.15.

31. The medical device system of claim 27, wherein:
the first wall thickness of the outer cannula is defined between (i) a first outer surface extending between the distal and proximal ends of the outer cannula and (ii) a first inner surface positioned opposite the first outer surface, the first outer surface having a first radius, and
the outer cannula includes a second outer surface that is connected to the first outer surface and extends between the distal and proximal ends of the outer cannula, the second outer surface having a second radius that is less than the first radius.

32. The medical device system of claim 31, wherein:
the outer cannula includes a second inner surface that is connected to the first inner surface and is positioned opposite the second outer surface, and
the first inner surface of the outer cannula defines a central section of the lumen, and
the second inner surface of the outer cannula defines an outer section of the lumen that opens into the central section.

* * * * *